(12) United States Patent
Novick

(10) Patent No.: US 10,463,545 B2
(45) Date of Patent: Nov. 5, 2019

(54) HUMAN JOINT PROTECTION SYSTEM

(71) Applicant: Walter R. Novick, Vail, CO (US)

(72) Inventor: Walter R. Novick, Vail, CO (US)

(73) Assignee: Walter R. Novick, Vail, CO (US)

( * ) Notice: Subject to any disclaimer, the term of this patent is extended or adjusted under 35 U.S.C. 154(b) by 721 days.

(21) Appl. No.: 14/682,790

(22) Filed: Apr. 9, 2015

(65) Prior Publication Data

US 2015/0290046 A1    Oct. 15, 2015

Related U.S. Application Data

(60) Provisional application No. 61/977,915, filed on Apr. 10, 2014.

(51) Int. Cl.
*A61F 5/00*        (2006.01)
*A61F 13/06*       (2006.01)
*A61F 13/00*       (2006.01)

(52) U.S. Cl.
CPC ...... *A61F 13/061* (2013.01); *A61F 13/00017* (2013.01); *A61F 13/00029* (2013.01)

(58) Field of Classification Search
CPC ...... A61F 5/0102; A61F 5/0106; A61F 5/013; A61F 5/0118; A61F 5/0123; A61F 5/0585; A61F 13/00017; A61F 13/00021; A61F 13/00029; A61F 13/00038; A61F 13/061; A61F 13/101; A61F 7/02; A61F 7/08; A41D 13/06; A41D 13/065; A63B 71/1225
USPC ...... 602/12, 14, 62, 75, 79, 20–27; 128/882, 128/892; 2/22, 24, 62; 442/59, 304, 181, 442/327, 320
See application file for complete search history.

(56) References Cited

U.S. PATENT DOCUMENTS

| | | | | |
|---|---|---|---|---|
| 4,278,079 A * | 7/1981 | Simhoni | ............... | A61F 13/069 128/892 |
| 4,409,975 A * | 10/1983 | Simhoni | ............... | A61F 13/069 128/892 |
| 6,199,234 B1 * | 3/2001 | Srour | ................. | A47C 27/146 5/716 |
| 6,279,160 B1 * | 8/2001 | Chen | .................... | A41D 13/065 2/24 |
| 7,975,634 B1 * | 7/2011 | Dugan | ................. | A41D 13/065 112/475.06 |
| 8,628,488 B2 * | 1/2014 | Serola | ................ | A61B 17/1325 128/846 |
| 2004/0134501 A1 * | 7/2004 | Hargis | ................ | A61F 5/0109 128/882 |
| 2012/0227150 A1 * | 9/2012 | Brown | ................. | A41D 13/065 2/24 |

(Continued)

*Primary Examiner* — Victoria J Hicks
(74) *Attorney, Agent, or Firm* — Leydig, Voit & Mayer, Ltd.

(57) ABSTRACT

A device is described that is configured to protect a joint of a wearer. The device includes a device cover structure having an interior surface of phase change fabric material that is placed toward the wearer's joint and an exterior surface of unbroken loop fabric that comes in direct contact with external objects such as a mattress and/or other parts of the users body or that of another person while in their preferred position for sleeping, resting or reclining. The device also includes flexible elastic wraps for securing the device cover. The Device furthermore includes one or more protective pads inserted into a pocket formed in the device cover structure.

18 Claims, 18 Drawing Sheets

(56) References Cited

U.S. PATENT DOCUMENTS

| | | | |
|---|---|---|---|
| 2014/0123361 A1* | 5/2014 | Gudalis | A41D 13/0156 2/22 |
| 2014/0189926 A1* | 7/2014 | Gudalis | A41D 13/0156 2/16 |
| 2014/0330184 A1* | 11/2014 | Kilbey | A61F 5/0123 602/13 |
| 2015/0038891 A1 | 2/2015 | Lipton et al. | |

* cited by examiner

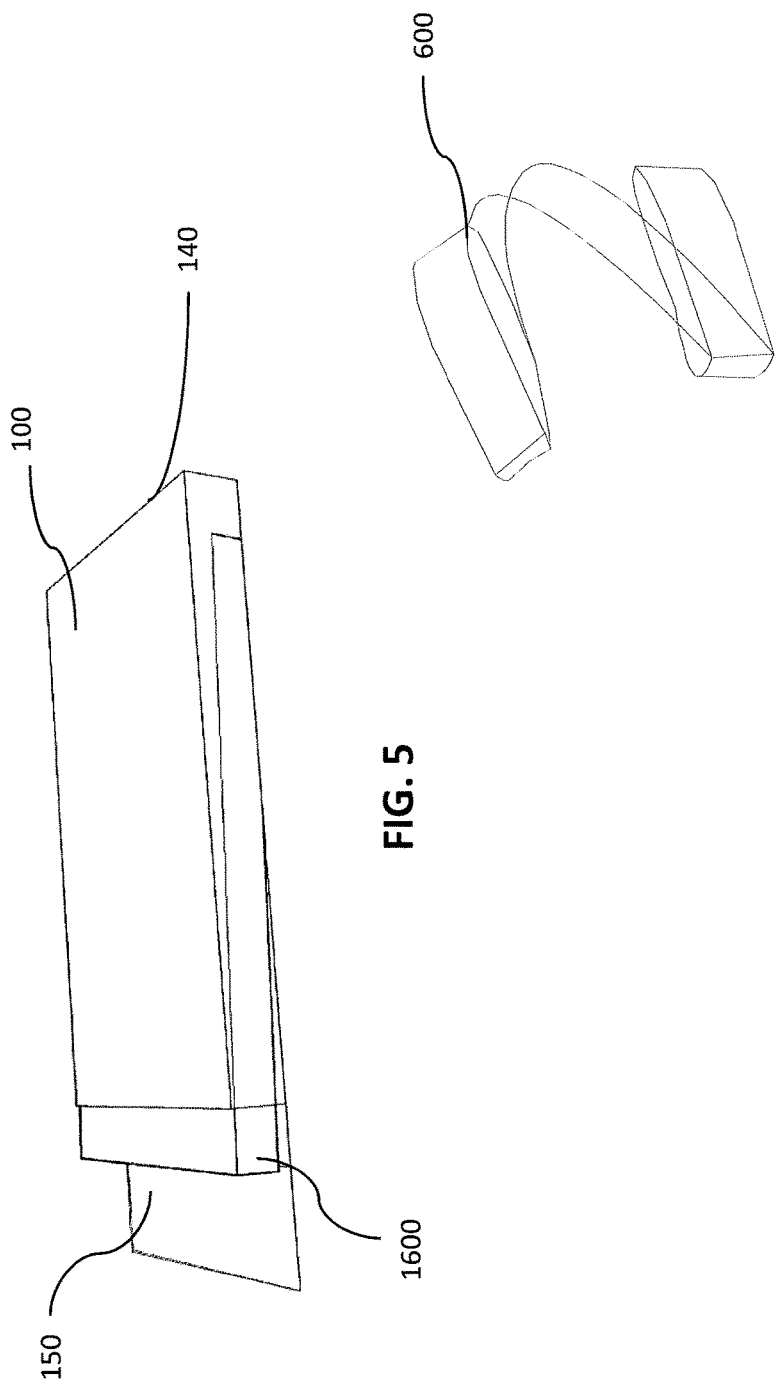

HUMAN JOINT PROTECTION SYSTEM

CROSS-REFERENCE TO RELATED APPLICATIONS

This patent application is the nonprovisional of U.S. Application Ser. No. 61/977,915, filed Apr. 10, 2014, the contents of which are expressly incorporated herein by reference in their entirety, including any references therein.

TECHNOLOGICAL AREA

The present invention generally relates to devices, apparatuses and equipment generally configured to be wrapped around a body extremity, such as an arm or leg, to offer a degree of support, comfort and/or protection in the vicinity of a joint. More particularly, the present invention is incorporated into a protective, padded, wrappable and adjustably secured knee guard providing comfort and protection to a wearer while in a resting, reclined, and/or sleeping position.

BACKGROUND OF THE INVENTION

Joint pain is a common musculoskeletal symptom that may be either acute or chronic. This is generally caused by a variety of diseases, injuries, surgeries and disorders that affect the joints. Joint pain is a symptom that affects 90% of the general United States population at some point in life with sufficient severity to cause loss of sleep. Joint pain is a common reason for visits to orthopedic surgeons, and joint pain/injury is estimated to cost the American economy billions of dollars every year.

People experiencing joint pain may readily attest efforts to sleep, rest or recline in a preferred position can be fraught with challenges to achieving a non-painful long-term desirable/comfortable rest position. Such challenges are especially troubling in the case of a chronic condition like degenerative joint disease or an acute injury to the knee joint or post-surgery to repair such injury. Pain in the affected joint of a patient renders sleeping, resting or reclining in a preferred (e.g., side) position to be extremely difficult and in some cases impossible due to a tender/sensitive/injured part of the patient's joint coming into direct contact with a mattress and/or other parts of the patient's body or that of another person.

Devices for personal protective wear, such as devices worn for padding and protecting the body, are conventionally made of several components that are permanently connected together and often offered in one or several sizes to fit all. The adjustability of the devices employing such methods is limited, and they are lacking in their ability to provide the user customization of the fit, function and protection. Furthermore, the permanent nature of these assemblies represents a potential source of irritation and discomfort. Such limited adjustability of known devices makes the devices potentially bulkier than necessary, imperfect in their protection, tighter than necessary, and interfere with a user's ability to sleep in a preferred (e.g., side) position while wearing the protection device. Such protection devices also present a potentially difficult ordeal to put on/secure independently in the case of a user having a limited range of motion or strength.

Permanently assembled devices, such as neoprene knee and elbow sleeves, and less permanently connected protection/support devices are imperfect as they can restrict the natural flexion and bending of the joint, retain heat and absorb moisture making the device both restrictive and uncomfortable in use. The performance of such joint protection/support devices is also denigrated by a presence of fabrics and padding that tend to trap and retain heat—properties causing the devices, when worn during sleep, to feel uncomfortable (due to rubbing/scratching) and uncomfortably warm when worn during periods of sleep to protect a particular part of the joint from damage do to direct contact with another hard object (e.g., the inside of an opposite knee).

Finally, as alluded to above, known protection devices potentially force users to abandon a preferred position for sleeping, resting or reclining because a protection device is not structurally/functionally configured to protect both sides and a front of the knee joint from direct contact with: a mattress, other parts of the user's body, and/or body parts of another person. The importance of a protection device enabling a user to assume a preferred side or face down sleeping position has been confirmed by research showing that a vast majority of people cite their preferred sleeping position to be on the side or stomach.

Given the observed shortcomings summarized above, known protection devices can potentially exhibit one or more of the following characteristics: poor fit, restrict flexion, limit bending and stretching of an extremity, excessive heat retention, moisture retention, inadequate protection of the sides and front of a joint from contact with a mattress, other body parts of the user, and/or another person. Additionally, wearing of some protection devices potentially requires changing a preferred position while sleeping, resting or reclining to experience a benefit of the protection device. As a result, many protection devices, when worn at night do not accommodate usage while sleeping in a preferred side or stomach position.

SUMMARY OF THE INVENTION

A joint protection device is described herein that is configured to protect a joint of a wearer, in particular a knee joint of the wearer. The joint protection device includes an interior device cover structure comprising a fabric sheet incorporating a ceramic fiber phase change material and having a moisture wicking property, wherein during use the interior device cover structure is placed toward a joint of the wearer. The joint protection device furthermore includes an exterior device cover structure comprising unbroken loop fabric. The exterior device cover structure and the interior device cover structure are joined along edges to form a pocket. A flexible elastic wrap is provided by the device to facilitate securing the joint protection device against a leg of the wearer. Moreover, the joint protection device includes at least one heat dissipating protective pad occupying the pocket such that while the joint protection device is secured against the knee of the wearer, the joint protection device surrounds the knee to provide protection against forces exerted by external objects on protected parts of the knee.

BRIEF DESCRIPTION OF THE DRAWINGS

Still other advantages of described embodiments will become readily apparent to those skilled in the art from the following detailed description, wherein the preferred embodiments of the invention are shown and described, simply by way of illustration of the best mode contemplated of carrying out the invention. As will be realized, the invention is capable of other and different embodiments, and its several details are capable of modifications in various obvious respects, all without departing from the invention and in accordance with the accompanying drawings illustrating a preferred embodiment of the invention, wherein like parts are identified by like reference symbols in each of the views, and wherein:

FIG. 2) including filamentary fastening hook tabs;

FIG. 5 illustratively depicts an exemplary configuration for a heat dissipating molded pad inserted in a pocket formed by stitched covers of the exterior device cover structure;

FIG. 6 illustratively depicts a configuration of the long flexible strap when wrapped around a knee joint to secure the joint protection device and fastened to the unbroken loop fabric material of the exterior cover structure using filamentary fastening hook tabs;

DETAILED DESCRIPTION OF DRAWINGS

Figure 1:
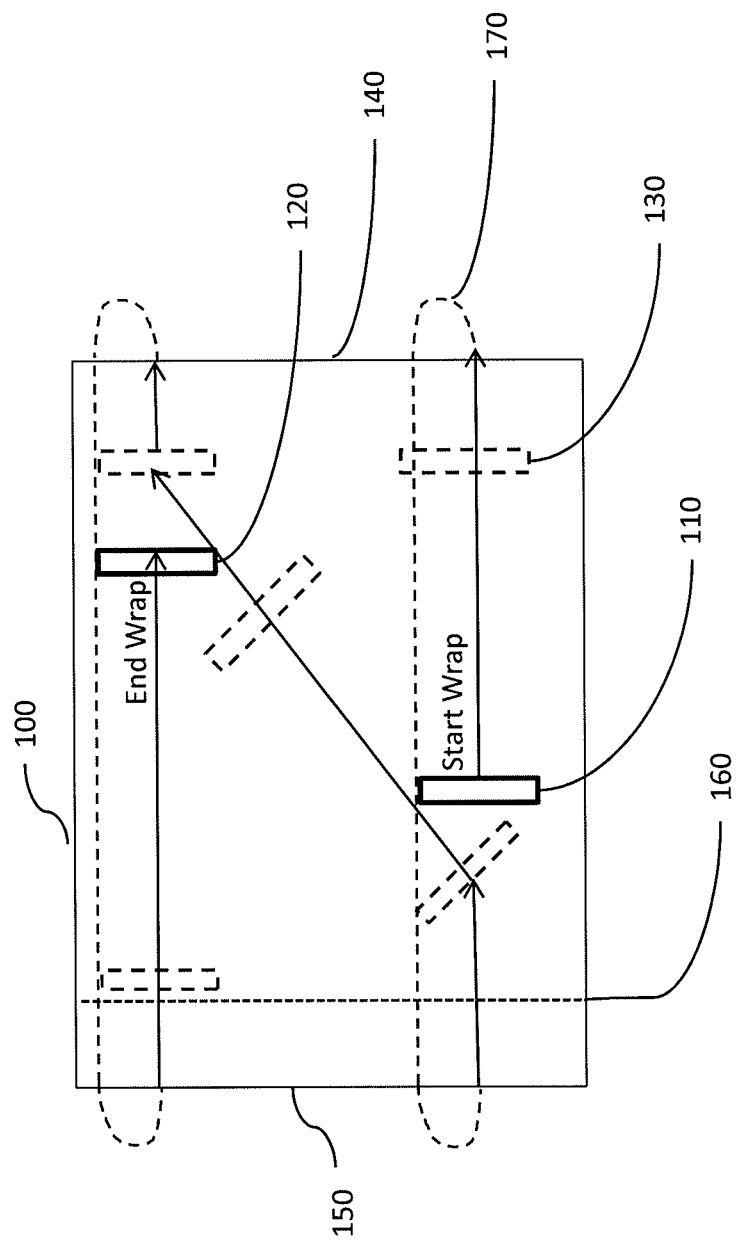
FIG. 1 is an exterior view of a joint protection device constructed according to the invention, with filamentary fastening and several alignment components sewn to the device cover structure and show the direction of the flexible elastic wrap for purposes of illustration.

Before commencing a detailed description of the figures that provide illustrative examples of a new protection device for a human extremity joint (e.g. a knee), a short summary of the illustrative embodiments is provided. In the illustrative examples, an improved securable, padded protective body joint guard/wrap is described in various embodiments that address several, if not all, shortcomings described herein above. Additionally, the exemplary protection devices provide advantages over known devices designed to protect, support and enwrap a human joint (e.g. a knee) to facilitate/aid a healing process after an injury and/or surgery.

The described joint protection system includes a heat-expelling/dissipating molded pad element, a removable/adjustable securable strap, and a cover sleeve including a built-in pocket configured to removably/interchangeably receive the molded pad element. The molded pad element, securable strap, and cover sleeve are non-permanently assembled components that facilitate separation and replacement of each distinct component by a user without damaging any individual component (e.g., removing stitching, separating sealed together/bonded layers, etc.). Such non-permanent assembly furthermore facilitates providing a wide variety of configurations that are quickly and easily customized in a matter of seconds in accordance with particular needs/preferences of the wearer.

The heat-expelling pads and cover are flexible and highly configurable to fit a wide range of configurations when positioning the wrappable joint protection device around/against/about human anatomy, exhibiting a variety of anatomical dimensions and shapes, for a joint that is to be protected. The protection device is provided in the form a kit that may include molded pads that vary in shape, size (including thickness) and density. The combination of highly adjustable strap positioning, pocket, and multiple pads (selectively inserted within the pocket) facilitates a high degree of customizability and adaptability to accommodate wearers of various height, weight, sex, medical condition and dimensions body part(s) in need of protection. The described joint protection system incorporates secure detachable fastening straps that facilitate alignment of a cooling, moisture wicking device cover structure in the form of a fabric incorporating phase change material. Phase change materials, in the form of ceramic fiber for integration into a woven fabric sheet, exhibit the property of absorbing excess heat in a vicinity of the material and releasing stored heat in response to relative cool temperatures in the vicinity of the phase change material. An example of such fabric incorporating phase change material is OUTLAST fabric (e.g., Texolinni OUTLAST 415A).

The pocket formed within the cover structure holds user selected heat-dissipating protective molded pads. The cover structure and associated detachable fastening straps render the joint protection device well suited for customizing the protection of the side and top of a knee joint without interfering with one's ability to sleep, rest or recline in a preferred position while still allowing for natural flexion, bending and stretching of the knee joint when wearing the joint protection device. The fabric making up the inner covering (placed against the wearer's knee) may be implemented using a breathable wicking material, including phase change material ceramic-fiber based woven fabrics, to enable the wearer's skin/body part to remain cool, dry and comfortable in locations where the joint protection device covers the wearer's knee, while preventing direct contact of the joint with another object such as, for example, a mattress and/or other parts of the wearer or another person.

The described joint protection device system, when secured to a knee, exhibits the properties of secure fastening, flexibility, pliability, and alignment of a padded protection device providing a cooling, moisture wicking device cover structure interface, and furthermore includes phase change material for regulating surface skin temperature through the absorption and release of heat. The joint protection device system holds a user customizable protective pad set including insertable/removable pads of various degrees of thickness and dimensions. The protective pad set includes a primary pad comprising a memory foam material having a convoluted surface including convex and concave areas forming air gaps that may accommodate the convex bulge of the patella, and provide ample airflow around the joint. The pad sets, including multiple protective pads of various sizes, shapes, densities, and degrees of stiffness/flexibility facilitate customizing the protection provided by the joint protection device of the side and top of the knee joint of the wearer without interfering with the wearer's sleep or ability to rest or recline in a preferred position. The protection device provides a degree of assurance to the wearer that a suitably high level of protection to an injured site is provided while permitting natural flexion, bending and stretching of a knee/leg when wearing the protection device. The fabric interface and foam padding enable a wearer to remain cool, dry and comfortable while using the protection device.

Embodiments of the joint protection device exhibit one or more of the following features:
1. Flexible, adjustable, releasable straps to self align the pads on the joint and ensure proper pad fixation against a user;
2. A multiple pad set comprising a choice of convoluted and non-convoluted molded pads with a varying degree of indentation force deflection (IFD) ratings to render a customizable level of protection and comfort for a wearer;
3. An exterior device cover structure including an unbroken loop fabric comprising a materials that is releasably graspable by a filamentary hook tab anywhere on an surface (when secured to a knee) for a customizable fit around/against a knee;
4. A high level of permitted flexion and freedom to bend a knee and stretch a leg—arising from an open back design and highly flexible protective pads;
5. Phase change material incorporated into the fabric of the cover structure including a pocket configured to hold the pads and exhibiting properties suitable for dissipating heat and evaporating moisture;
6. Heat dissipating molded pads to reduce heat retention and ensure comfort;
7. A wrappable device structure that, when secured to the wearer, protects the sides and top of the joint (knee) so that a majority of wearers do not have to alter their preferred position for sleeping, resting or reclining; and
8. wrap-around configuration provides cushioned contact in the event of the wearer coming in contact with a mattress and/or body parts of the wearer or another person.

Embodiments of the described invention provide a joint protection system that overcomes many, if not all, of the problems of prior devices mentioned in the background above, and thus provides several advantages that are not contemplated or possible when using the previously available devices. The described joint protection device, when secured to a wearer's knee, provides cool, dry, comfortable protection of the joint during rest or even non-strenuous movement. The protection device comprises a multi-piece set of pads to provide molded and highly customizable configuration of the protection device around a wearer's knee to allow for natural flexion, bending and stretching of the knee joint so that a user may sleep comfortably in a preferred position, without blocking heat and moisture flow from the wearer's skin surface covered by the wrapped protection device.

Further, in a described embodiment and typical secured configuration, the protection device provides flexible/adjustable padded protection on the front and sides of a wearer's knee joint while permitting exposure of the wearer's skin in the back of the knee to permit flexion, bending and enhanced heat release in the vicinity of the knee joint (counter excessive restriction of joint movement or heat buildup) while a wearer sleeps in a preferred position.

To this end, the protection device's cover structure including a pocket for receiving a selected pad or pads, selectable multi-pad sets, associated fastening strap(s) and alignment components aid proper positioning of the joint protection system in order to provide secure, comfortable, and highly customizable padding to an injured knee joint or any other body joint that needs protection while the user sleeps, rests or reclines.

A described particular embodiment provides a joint protection device having a supporting device cover structure including a formed pocket/compartment and one or more protective pads providing for the customization of a degree of protection provided by the user-selected/customized set of protective pads inserted within the pocket of the protection device cover structure. Moreover, filamentary fastening hook strips and complementary looped fabric (facilitating a releasable attachment of the straps to the outer fabric of the protection device facilitate proper securing the protection device around/next to the part of the joint for which protection is needed/desired.

A described exemplary embodiment provides a joint protection device that properly aligns one or more straps and protective pads against the joint with the desired pressure through use of wrap alignment slots/tabs and a flexible elastic warp.

A described exemplary embodiment provides a joint protection device that also properly aligns the wrap and protective pads against the body with the desired pressure to using an outside cover made of unbroken loop (UBL) fabric that releaseably engages hook filamentary fiber fasteners and aligning without use of wrap alignment slots/tabs and the filamentary fixation tabs.

The described exemplary embodiments provide a joint protection system for a joint such as, for example, a human knee. The described embodiments of the joint protection system include a cooling, moisture wicking device cover structure made with phase change material for placement against a wearer when the device is in a wrapped configuration, a selection of multiple protective heat dissipating molded pads selectively positioned within a pocket/chamber formed within the protection device, fastening and alignment capability and/or components that together with the flexible elastic wrap provide a highly customizable fit, function and level of protection of the joint adjustable by a wearer so that the wearer can sleep comfortably in a preferred sleeping position without the device shifting out of place. The above advantages are each achieved while also permitting natural knee/leg flexion, bending and stretching and remaining cool, dry and comfortable to the touch when wearing the device.

Embodiments also include a method of protecting a joint while sleeping that utilizes a system having sufficient padding and protection of the joint on a front and sides along with an open back to allow for natural flexion, bending and stretching so that the user may sleep comfortably in their preferred position without restriction, or a buildup of heat, moisture or pressure points.

An exemplary embodiment of the protection device includes a protection device cover structure constructed from phase change fabric material that incorporates advanced heat and moisture transfer through evaporative cooling. The phase change fabric material offers enhanced breathability, heat dissipation, and moisture-wicking properties to keep the affected area of the device wearer feeling cool, dry and comfortable.

A particular exemplary embodiment provides a joint protection device in which the component parts are fastened together by filamentary fastening fiber patches, thereby providing a wide range of adjustability and increased comfort with a customized fit. Critical fixation is achieved above the knee at a point above a head of the femur and below the knee around the patella tendon and below the head of the tibia to ensure that the joint protection device remains comfortable and does not shift in position while in use—yet can be adjusted for a customized fit.

An additional described exemplary embodiment is a protection system including a set of heat dissipating molded pads of various properties (e.g. size, location, density, shape, etc.) supporting a variety of configurations that are customizable by the user. The pads are formed to conform to user anatomy to and support secure/comfortable protection for the joint that is protected. As such, the protection device is highly configurable to accommodate users that vary in height, weight, sex, medical condition and dimensions of the body part(s) in need of padded protection.

Exemplary embodiments of the protection device provide protection and comfort to sufferers of knee joint pain arising from, for example, a chronic condition like degenerative joint disease, or an acute injury to the knee or surgery to repair the knee, and prevent the onset of such joint pain in non-sufferers.

Furthermore, described illustrative embodiments provide protection on the front and sides of the joint while remaining open in the back to allow for flexion and bending while sleeping in the users preferred position. To this end, the device cover structure with its fastening and alignment components and the flexible elastic wrap aids in proper positioning of the joint protection system in order to provide secure direct padding and protection to the joint that needs protection.

A joint protection device described herein is well adapted for being kept clean and sanitary, and includes a washable cover structure including a pocket/chamber formed therein for holding one or multiple removable/replaceable heat dissipating molded pads.

Illustrative examples are now described more fully in detail with reference to the accompanying drawings, in which the exemplary/illustrative embodiments are shown. This invention should not, however, be construed as limited to the embodiments set forth herein; rather, they are provided so that this disclosure will be complete and will fully convey the scope of the invention to those skilled in the art.

Turning now to the drawings, FIG. 1 illustratively depicts the exterior side piece of an exemplary joint protection device including filamentary fastening and alignment components sewn to an exterior device cover structure 100 forming an exterior portion of the joint protection device. Arrows are provided that show a direction of wrapping a flexible elastic wrap depicted in FIGS. 2 and 6. The exterior device cover structure 100, comprising two overlapping sheets of fabric material 140 and 150 (forming a slot 160 through which padding is inserted/removed), is joined with an interior device cover structure 180 (see FIG. 3a) to form a pocket. The resulting slotted pocket accommodates/holds a selection/combination of one or more heat dissipating pads (see, FIG. 17 pads 1710, 1720 and 1730) having a variety of indentation force deflection (IFD) ratings. The resulting pad holding structure is held in place by a long flexible elastic wrap (see e.g., FIG. 2 wrap 200) to pad and protect a knee of a wearer while securely wrapped and secured on a knee joint (see FIG. 7).

Figure 3A:
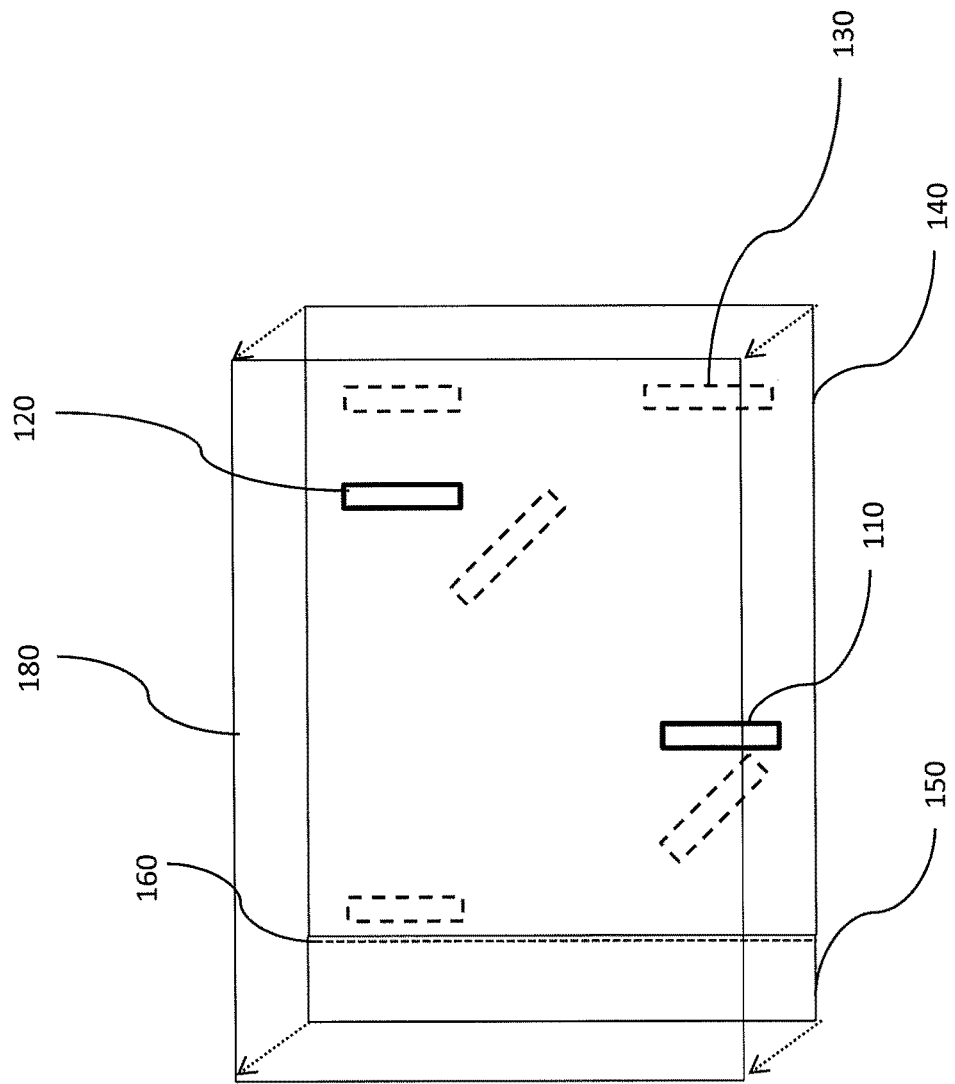
FIG. 3a is an exploded view of the cover structure of the device depicted in FIG. 1.

In an exemplary embodiment, the interior (against the knee) surface of the joint protection device is formed by the interior device cover structure 180 depicted in FIG. 3a, and the exterior device cover structure 100 (facing away from the knee) of the joint protection device is formed by the overlapping sheets of fabric material 140 and 150 (forming the slot 160). The interior device cover structure 180 is made of at least one piece of cooling moisture wicking fabric material. The exterior device cover structure 100, in the illustrative example, is constructed from two overlapping sheets of fabric material 140 and 150 that form a slot 160 (in FIG. 1). The non-slot edges of the sheets 140 and 150 are sewn/bonded together with the interior device cover structure 180 to form a pocket.

With continued reference to FIG. 1, the exterior device cover structure 100 exterior surface includes two filamentary fastening tabs 110 and 120 with a loop surface as part of the attachment system and alignment tabs (e.g., tab 130) through which the strap 200 passes to ensure that the interior of the device cover structure (facing the knee surface) is properly secured to the leg/knee joint of a wearer so as to remain in place while the wearer sleeps, rests, reclines in a preferred position while allowing for natural flexion, bending and stretching of the wearer's leg/knee when wearing the protection device and remaining cool, dry and comfortable to the touch.

Thus, in summary, FIG. 1 is an exterior view of a joint protection device including filamentary fastening tabs and several alignment components sewn to the protection device cover structure. In FIG. 1 the following elements are indicated:

- 100—exterior device cover structure;
- 110—Filamentary fastening loop tab to attach one end of wrap 200;
- 120—Filamentary fastening loop tab to attach opposite end of wrap 200;
- 130—One of five identified wrap alignment tabs;
- 140—Right side sheet of device cover structure 100;
- 150—Left side sheet of device cover structure 100;
- 160—Slot, formed by overlapping edges of sheets 140 and 150, for the insertion of protective foam pads into the device cover structure pocket formed between the exterior device cover structure 100 and the interior device cover structure 180; and
- 170—Path of the flexible elastic wrap around the device cover structure.

The use of two overlapping sheets 140 and 150, as opposed to a single sheet (similar to the interior device cover structure 180), facilitates secure insertion of the pad material within the joint protection device by trapping both ends of such pads when inserted within the pocket. However, in alternative embodiments a single sheet is used instead of the illustratively depicted multiple sheets 140 and 150 for the exterior device cover structure. Additionally, in yet other embodiments, the interior device cover structure 180 comprises two sheets and the exterior device cover structure 100 consists of a single sheet.

Figure 2:
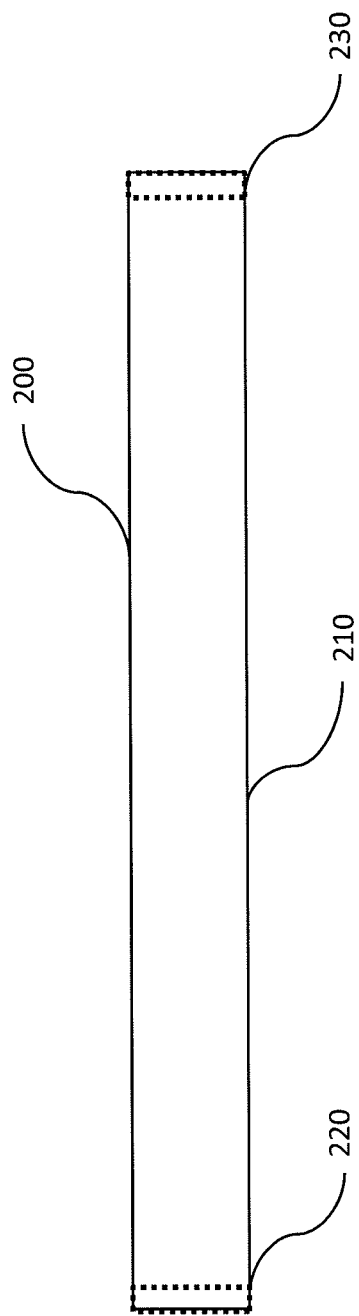
FIG. 2 is a long flexible elastic wrap with filamentary fastening hook tabs for securing the joint protection device of FIG. 1 around a joint (e.g. a knee)

FIG. 2 illustratively depicts the flexible elastic wrap 200 with filamentary fastening hook tabs 210 & 220 that securing the joint protection device, including the exterior device cover structure 100 holding one or more pads, inserted into the pocket via the slot 160, to the joint by affixing one end of the flexible elastic wrap 200 via the filamentary fastening hook tab 210 to the filamentary fastening loop tab 110 on the exterior device cover structure 100. The flexible elastic wrap 200 is threaded through the alignment tabs 130 on the exterior of the exterior device cover structure 100 and the opposite end of the flexible elastic with a filamentary fastening hook tab 220 is attached to the exterior of the device cover structure at the filamentary fastening loop tab 120 in accordance with the invention.

Thus, in summary, FIG. 2 depicts a long flexible elastic wrap with filamentary fastening hook tabs including:

- 200—Flexible elastic wrap with filamentary fastening hook tabs;
- 210—Flexible elastic wrap;
- 220—Filamentary fastening hook tab to attach one end of wrap to device cover structure; and
- 230—Filamentary fastening hook tab to attach opposite end of wrap device cover structure.

FIG. 3a is an exploded view (with arrows indicating the separation between parts) of the joint protection device including the interior device cover structure 180 and the exterior device cover structure 100 along with the filamentary fastening loop tabs 110 & 120 and alignment tabs 130 in accordance with the invention. Thus, FIG. 3a depicts, in an exploded view, a device cover structure including:

- 100—Exterior device cover structure;
- 110—Filamentary fastening loop material tab to attach one end of wrap 200;
- 120—Filamentary fastening loop material tab to attach the opposite end of wrap 200;
- 130—One of five wrap alignment tabs (indicated in dashed outlined rectangles);
- 140—Right side fabric sheet of exterior device cover structure 100;
- 150—Left side fabric of exterior device cover structure 100;
- 160—Slot between right and left side sheets 140 and 150 for the insertion of protective foam pads into the device cover structure; and
- 180—Interior device cover structure.

Figure 3C:
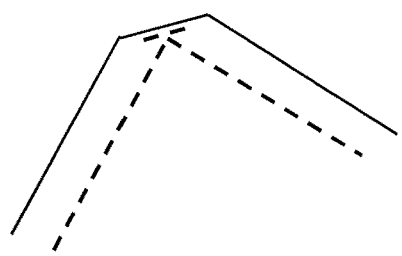
FIG. 3c illustratively depicts stitching providing additional reinforcement at corners of joined inside and outside device structure covers forming a pocket configured to receive/hold foam pad inserts for the joint protection device.
Figure 3B:
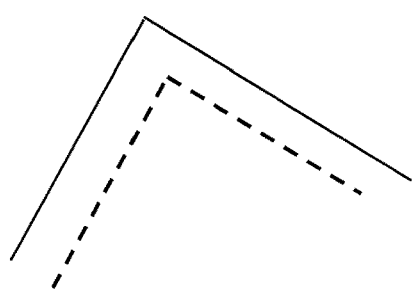
FIG. 3b illustratively depicts stitching for connecting inside and outside device structure covers to form a pocket configured to receive/hold foam pad inserts for the joint protection device.

FIG. 3b Illustrates the stitching connecting the interior device cover structure 180 and the exterior device cover structure 100 to form the complete joint protection device cover structure including the exterior slot 160, formed by the overlapping multiple sheets 140 and 150 of the exterior device cover structure 100, for the insertion of one or more of the protective foam pads 510. Such stitching is used on the perimeter of the joint protection device to form a pocket within which a selectable combination of pads (see FIG. 17, pad set including convoluted pad 1710, relatively thick flat pad 1720 and relatively thin flat pad 1730) are inserted via the slot 160.

Figure 17:
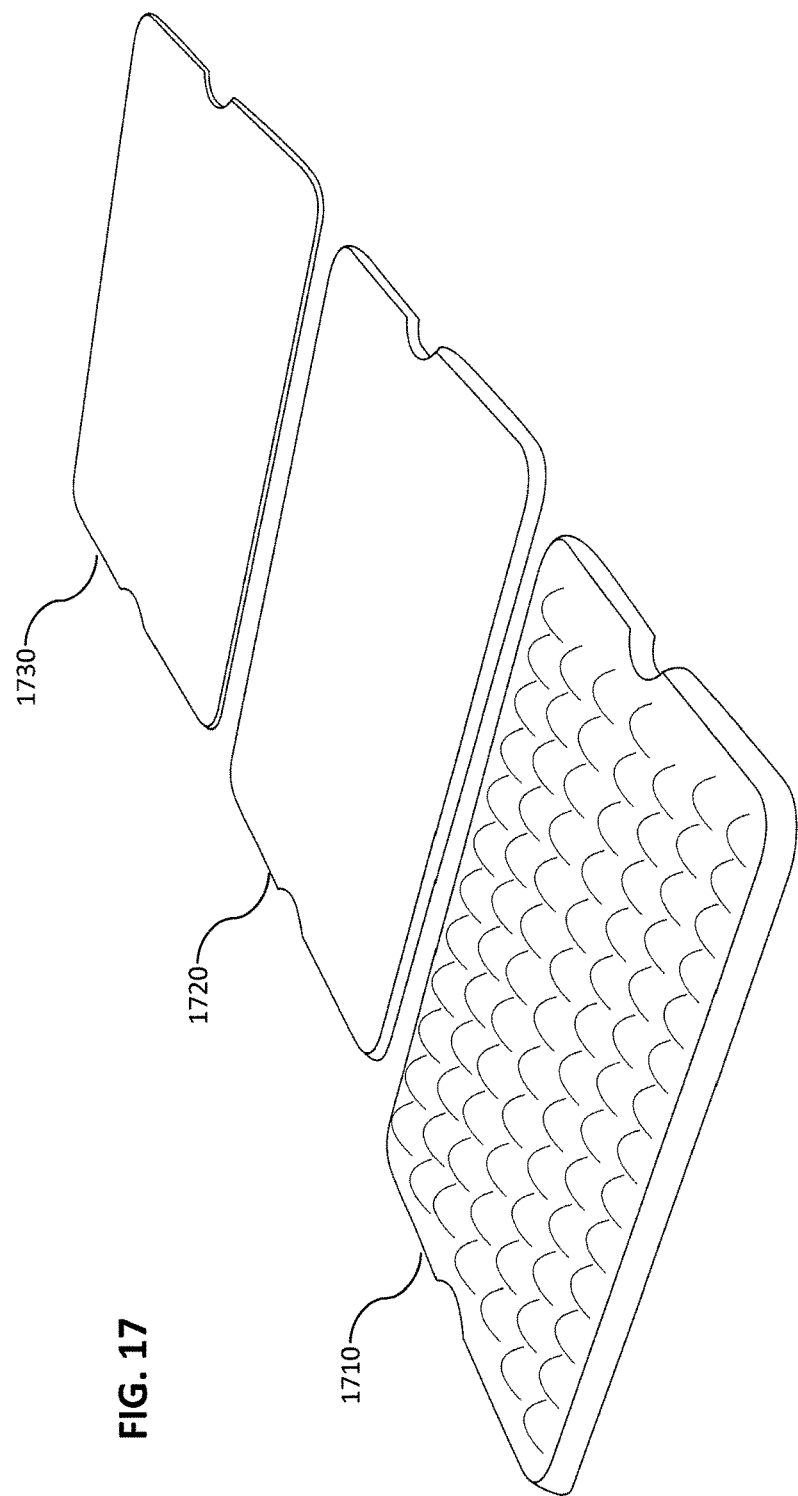
FIG. 17 illustratively depicts an isometric view of a set of three selectively/interchangeably inserted foam pads configured for placement in the pocket formed by the two joined fabric covers of the joint protection device to provide a customizable degree of protection of the covered knee from outside forces (such as the other knee of the device wearer)

FIG. 3c Illustrates, alternatively, corner reinforcement stitching connecting the interior device cover structure 180 and the exterior device cover structure 100 to form the complete joint protection device cover structure with the exterior slot 160 for the insertion of one or more of the protective foam pads (see FIG. 17, pad set including convoluted pad 1710, relatively thick flat pad 1720 and relatively thin flat pad 1730).

Figure 4:
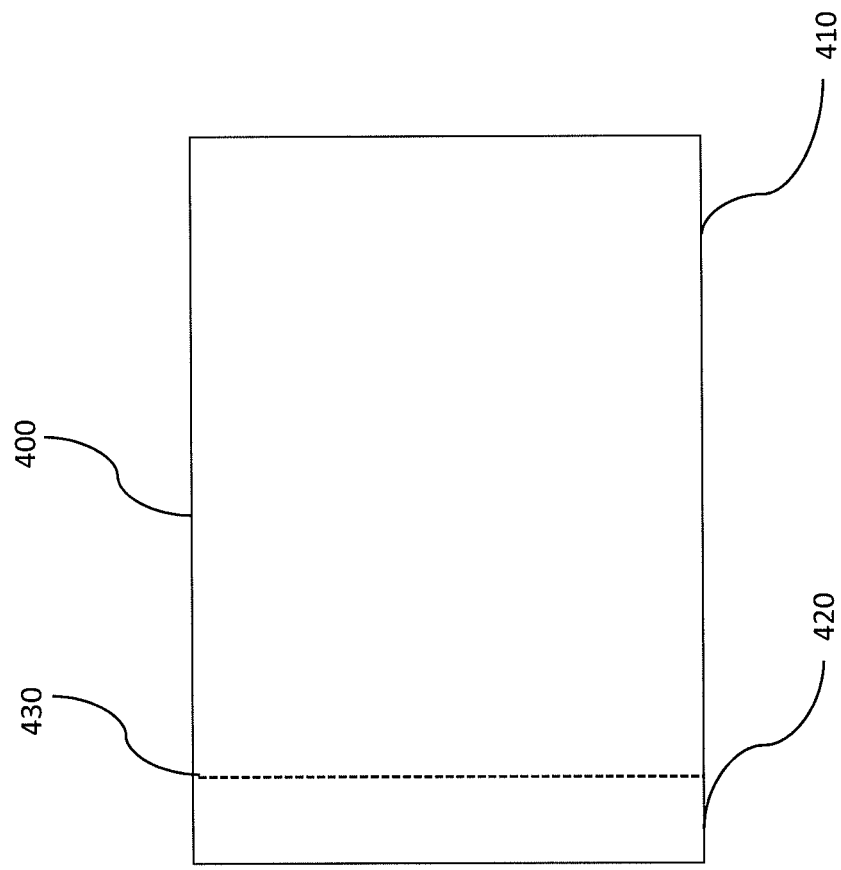
FIG. 4 illustratively depicts an exterior device cover, forming a pocket, structure made from unbroken loop fabric material suitable for complimentary use with inserted foam padding and a fastening strap (e.g.

FIG. 4 depicts an exterior device cover structure 400, forming a slot 430 by overlapping sheets 410 and 420 (corresponding to sheets 140 and 150 in FIG. 1). In the illustrative embodiment of the exterior device cover structure 400, the overlapping sheets 410 and 420 are made from unbroken loop fabric material suitable for complimentary use with inserted foam padding and a fastening strap (e.g. FIG. 2) including filamentary fastening hook tabs. In this case the fabric material of the exterior device cover structure 400 is suitable for engaging the filamentary fastening hook tabs 220 and 230. Therefore, the fastening hook tabs 210 & 220, which enable the user to secure the joint protection device around a wearer's knee joint, can be attached virtually anywhere on to the exterior device cover structure 400. The flexible elastic wrap 200 is wrapped around the knee joint in a "Z" pattern (see FIGS. 6 and 7) and the opposite ends containing the filamentary fastening hook tabs 210 and 220 are attached to the exterior device cover structure 400 anywhere the wearer desires.

Thus, in summary, FIG. 4 illustratively depicts the alternative embodiment wherein the originally described exterior device cover structure 100 comprising a fabric that is not suitable for engaging tabs 210 and 220 is replaced by the exterior device cover structure 400, including overlapping sheets 410 and 420 forming an opening at the slot 430 for insertion/removal of a selectable pad set.

FIG. 5 illustratively depicts the joint protection device including the exterior device cover structure 100 in a configuration with a pad 1600, which can be one or more pads (see FIG. 17 pads 1710, 1720 and 1730), inserted into the pocket having an opening at a point of overlap between sheets 140 and 150. After insertion, the pad 1600 would be moved to the left to trap the edge of pad 1600 under sheet 140.

FIG. 6 illustratively depicts the Z wrap pattern of the flexible elastic wrap 200 when the joint protection device is wrapped around a knee and secured by the wrap 200. This arrangement of the strap provides support for the joint protection device both above and below the knee joint. The connecting portion of the strap (between the upper and lower loops) ensures that the upper loop does not ride too high and the lower loop does not sag too low during flexing and bending of the knee joint while the device is secured to a wearer.

Figure 8:
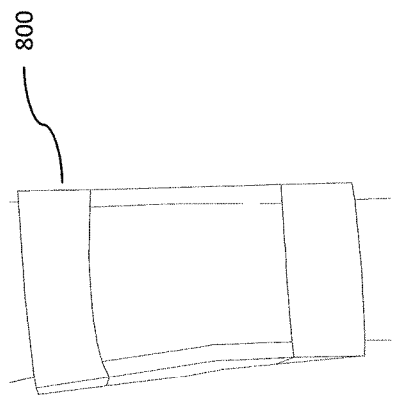
FIG. 8 illustratively depicts a rear view of the joint protection device in the secured and wrapped configuration on the knee joint (rear)
Figure 9:
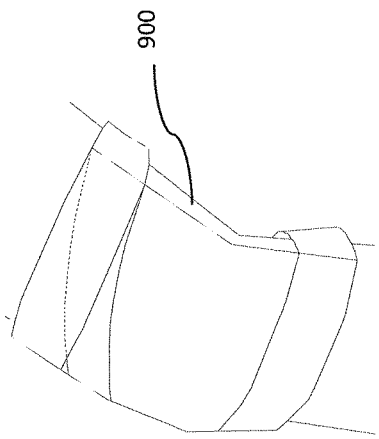
FIG. 9 illustratively depicts a side view of the joint protection device in the secured and wrapped configuration on the knee joint.
Figure 7:
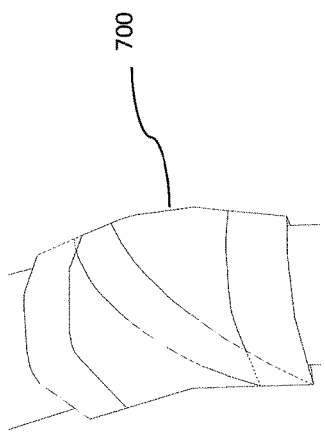
FIG. 7 illustratively depicts a front view of the joint protection device in a secured and wrapped configuration on a knee joint.

FIGS. 7, 8 and 9 illustratively depict the joint protection device in a typically wrapped configuration on a wearer's knee. The view 700 is of the front of the wrapped knee joint, the view 800 is of the rear view of the wearer's knee (note the open back area to enhance air flow and avoid under restriction of knee bending by leaving the back of the knee open, the view 900 is a side view of the wrapped knee joint.

Figure 10:
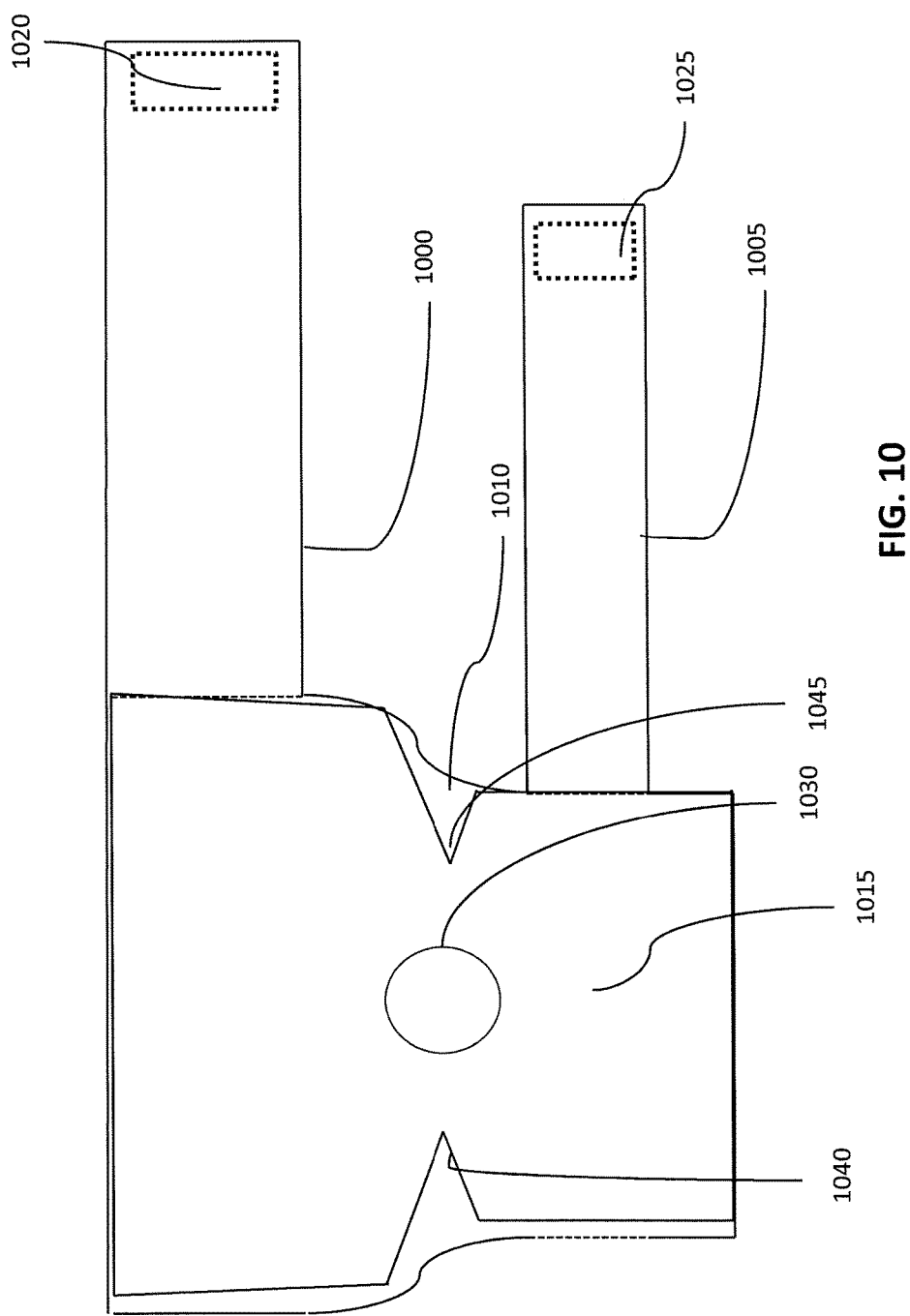
FIG. 10 illustratively depicts an interior surface view of an alternative embodiment of the joint protection device including two straps permanently connected on a fixed end, and having a free end including a patch of filamentary fastening hooks for engaging continuous loop fabric on an exterior cover of the joint protection device.
Figure 11:
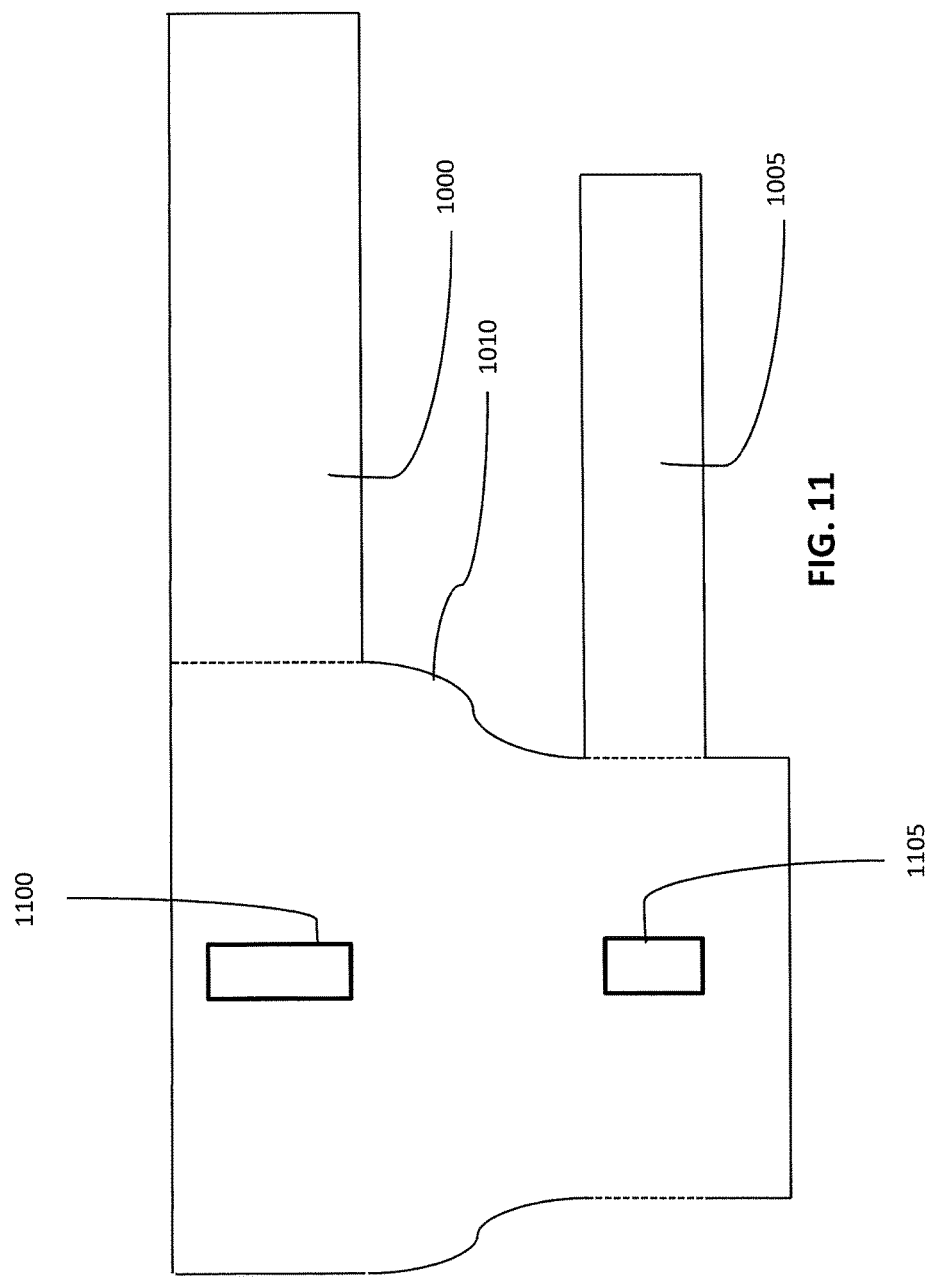
FIG. 11 is an external surface view of the joint protection device cover structure with integrated wraps.
Figure 12:
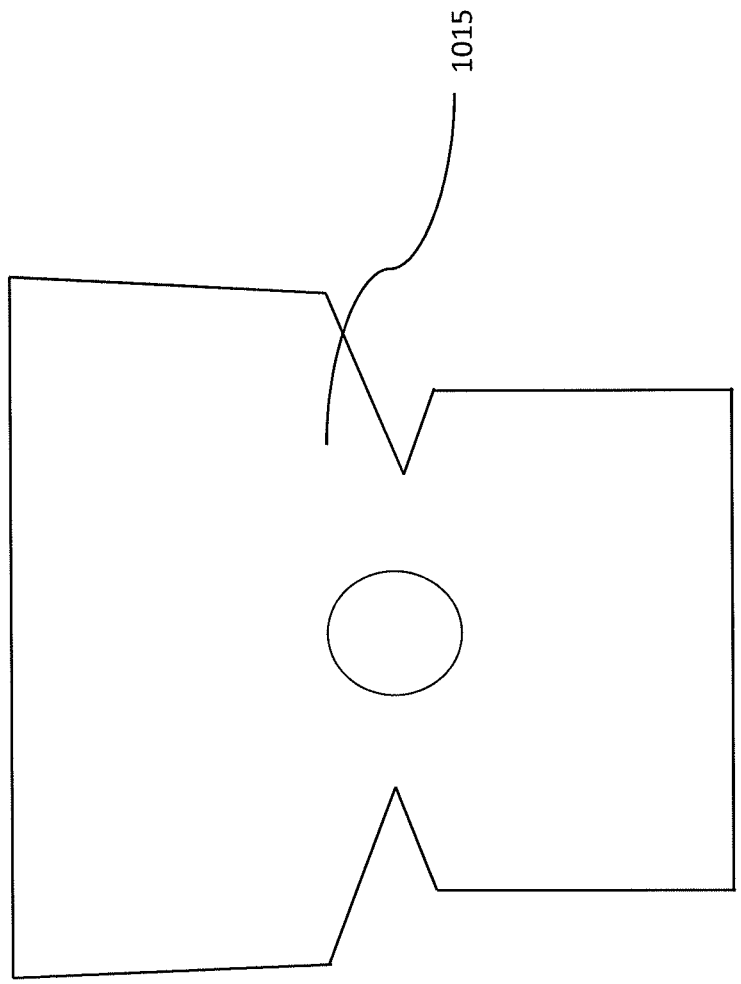
FIG. 12 is a top view of a heat dissipating molded pad with convoluted molded indentation for patella of the embodiment and view depicted in FIG. 10.
Figure 13:
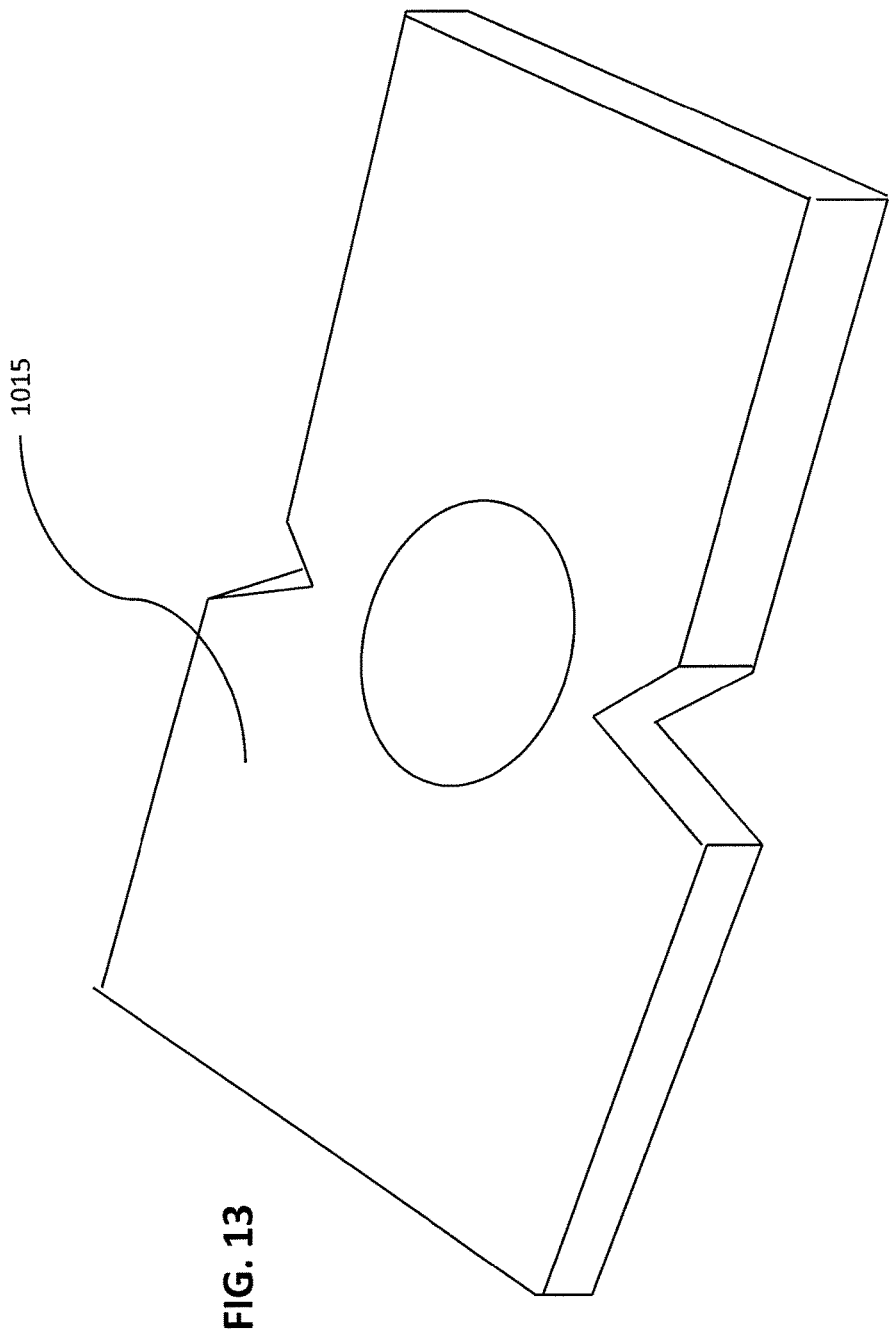
FIG. 13 is an isometric view of the heat dissipating molded pad with convoluted molded indentation for patella depicted in FIG. 12.

FIGS. 10, 11, 12 and 13 illustratively depict various views of an alternative design of the joint protection device wherein the wrap 200 is replaced by multiple fixed straps (e.g. straps 1000 and 1005) that are stitched/bonded to an exterior device cover structure 1010. In FIG. 10 an interior view of the joint protection device shows a surface of a molded pad 1015 that rests against the knee when placed in the wrapped configuration by a wearer. The molded pad 1015, by, way of example, is a heat dissipating material including a molded indentation 1030 to accommodate a patella. Additional fitting advantages are provided by opposing side cutouts 1040 and 1045 in the molded pad 1015 to facilitate bending of the molded pad 1015 with reduced binding at the edges. Strap 1000 includes a patch 1020 bearing filamentary hook material, and strap 1005 includes a patch 1025 bearing filamentary hook material. Additional views of the molded pad 1015 are provided, in isolation, in FIGS. 12 and 13.

Figure 14A:
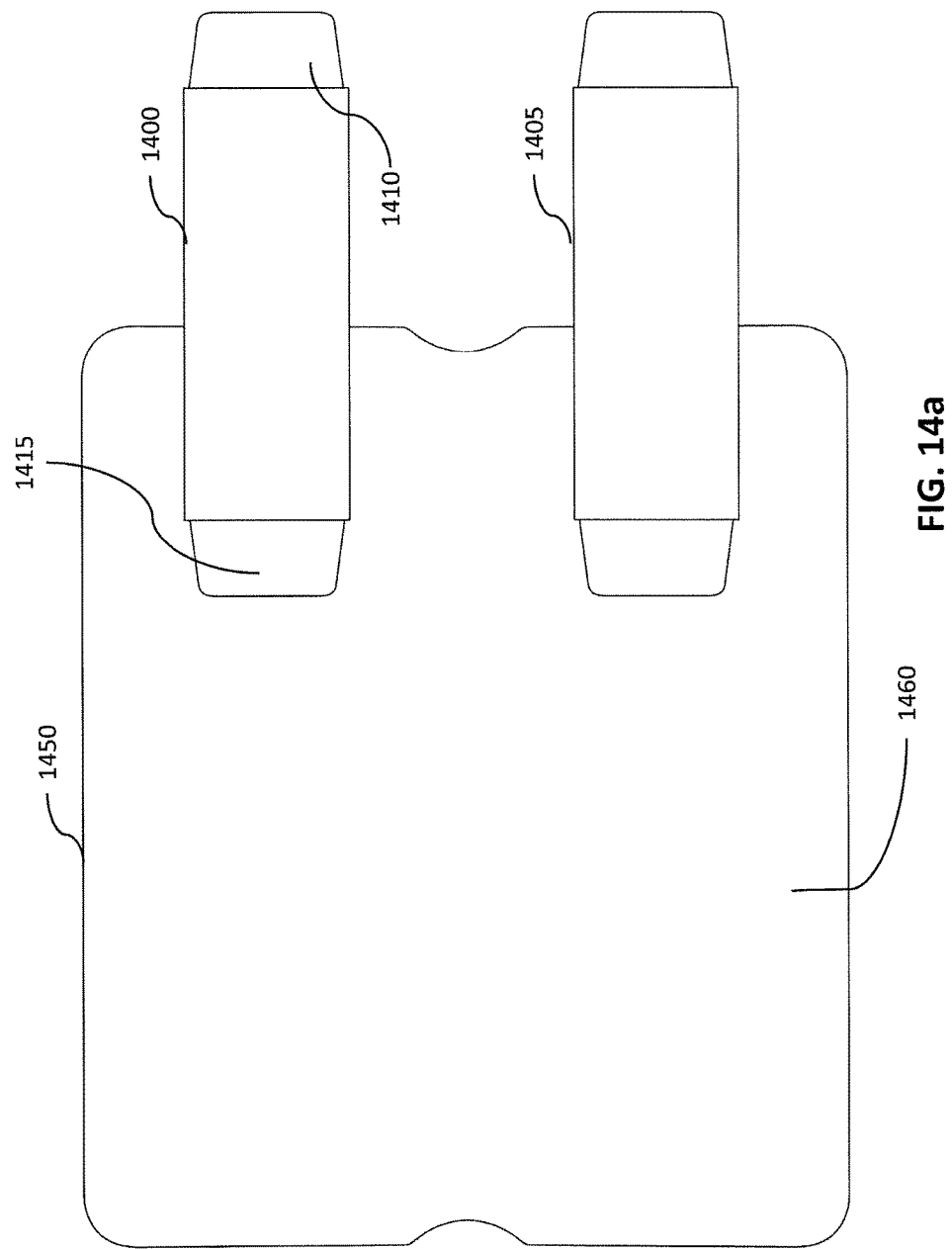
FIG. 14a illustratively depicts an external surface view of another exemplary embodiment of a joint protection device structure comprising a fabric outer cover and two detachable straps, each one of the two straps including at least two patches comprising filamentary fastening hooks configured to releasably engage the fabric outer cover to facilitate securely wrapping the protection device structure to/against/around a periphery of a joint.
Figure 14B:
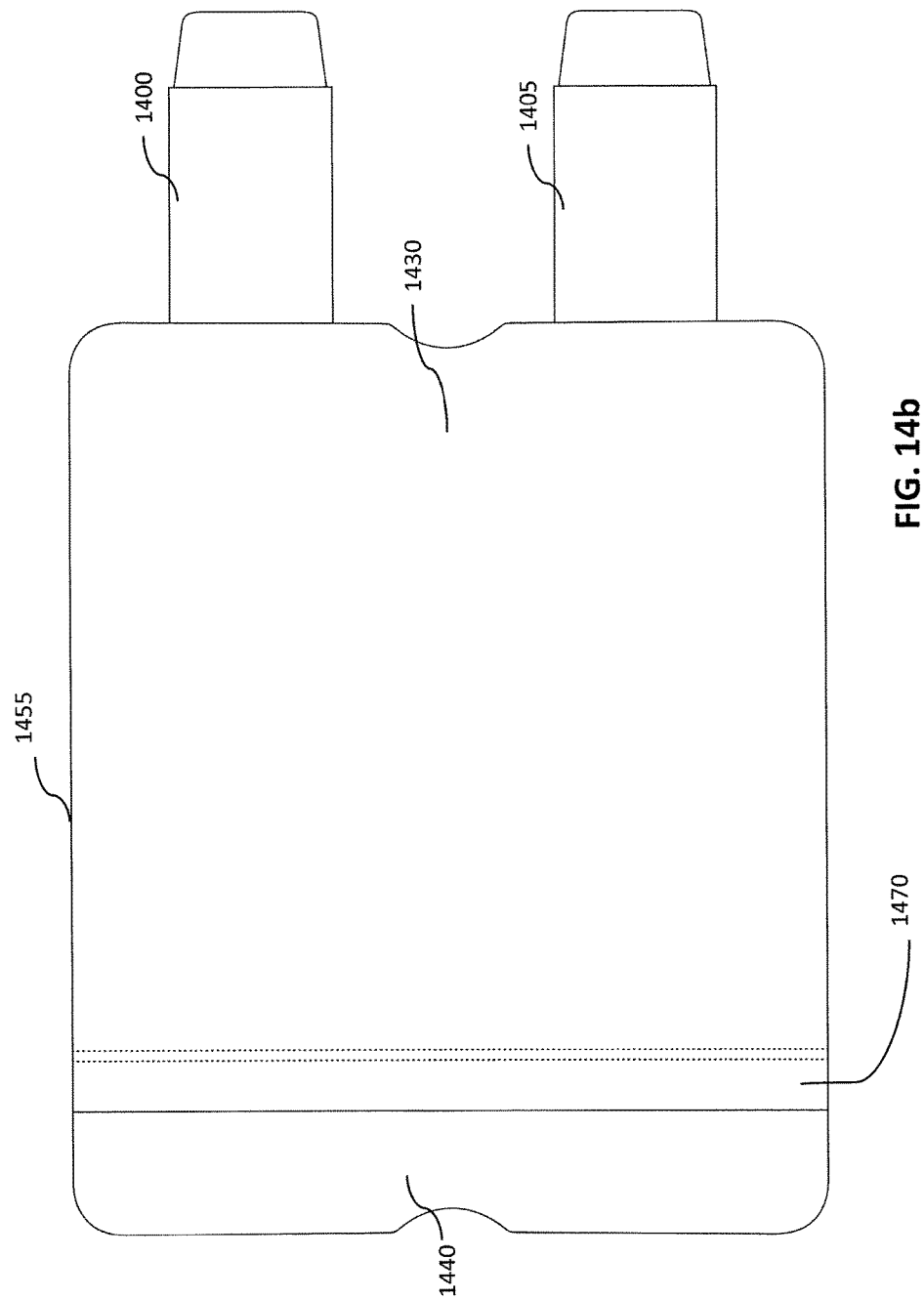
FIG. 14b illustratively depicts an opposite external surface view of the embodiment depicted in FIG. 14a to indicate a pocket opening formed by the outer covering layers on three sides and leaving at least a portion of a fourth side to facilitate insertion/removable of one or more foam/padding inserts.

Turning to FIGS. 14a and 14b, exterior and interior device cover structures (1450 and 1455, respectively) are depicted in accordance with yet another illustrative embodiment. In this embodiment, the single wrap 200 is replaced by two flexible elastic wraps 1400 and 1405. The elastic strap material of the wraps 1400 and 1405 is, for example, Elastic Rhode Island Knitting style 897-3 inch white elastic strap material. In the additional illustrative embodiment, an exterior device cover structure 1450 comprises a single fabric sheet 1460. The single fabric sheet 1460 is, for example, an unbroken loop fabric (e.g. Darlington Fasten-Air Unbroken Loop Fabric WW1432) which facilitates attachment of complementary filamentary fastening hook tabs (VELCRO HTH 810) on the flexible elastic wraps 1400 and 1405 (see e.g., tabs 1410 and 1415 of elastic wrap 1400) anywhere on the exterior device cover structure 1450. Thus, when securing the joint protection device to a knee, the device body is wrapped around the knee (on the front side), and the flexible elastic wrap 1400 is stretched across the backside of the knee. The tabs 1410 and 1415 are attached at opposing sides of the single fabric sheet 1460 (unbroken loop fabric material) to secure the device around the wearer's knee so as to remain in place while the user is sleeping, resting or reclining in their preferred sleeping position while allowing for natural flexion, bending and stretching when wearing the device and remaining cool, dry and comfortable to the touch.

Turning to FIG. 14b, a view is provided of the interior device cover structure 1455. The interior device cover structure 1455, in this embodiment, includes two sheets of fabric material 1430 and 1440 that overlap to form an insertion slot 1470. As previously noted, the fabric material making up the two sheets of fabric material 1430 and 1440 is moisture wicking fabric layer incorporating phase change material (e.g. Texolinni OUTLAST 415A fabric incorporating phase change ceramic fiber) for regulating skin temperature at the point of contact with the fabric material 1430 and 1440. Moreover, the insertion slot 1470 provides an opening for inserting and removing one or more of a selectable pad collection including, for example, the pads 1710, 1720, 1730. Examples of such foam pads are: Future Foam convoluted memory foam model numbers VO910, VS14400, and VS08300; and Future Foam 36125 grey polyurethane medical foam (for pads 1720 and 1730). It is further noted that pads 1710, 1720 and 1730 that are inserted within the protection device depicted in FIGS. 14a and 14b include notched/indented sides to reduce excessive compression of the pads when a knee bends while the device is secured to the knee.

Figure 14C:
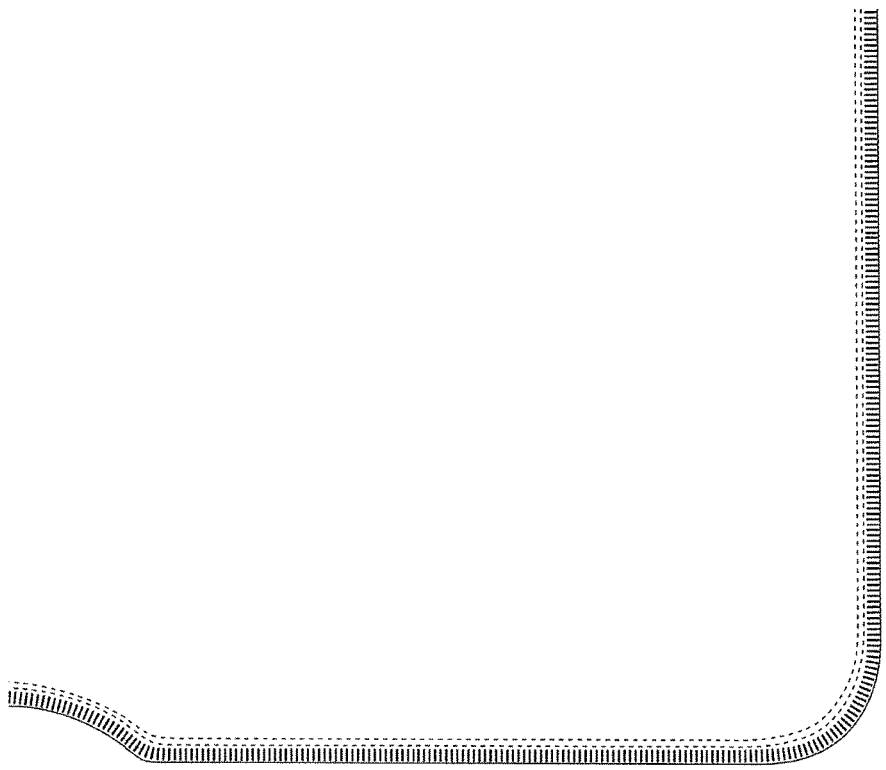
FIG. 14c illustratively depicts an exemplary stitching pattern connecting an outer fabric cover layer and an inner cover layer to form a pocket of the joint protection device.

Turning briefly to FIG. 14c an illustrative stitching pattern is provided for connecting the exterior device cover structure 1450 and interior of the device cover structure 1455 composed of a sides 1430 and 1440 to form the complete device cover structure including a pocket formed between the device cover structures 1450 and 1455, with the slot 1470 formed by the sheets 1430 and 1440 of the interior device structure 1455, to allow for the insertion of one or more of the protective foam pads 1710, 1720, 1730 depicted in FIG. 17. The particular choice of a combination of the pads (or a single pad) is selected by the wearer according to individual preferences and needs with regard to comfort and protection of the knee joint.

The protective device, as noted previously, including a pocket accessed via the slot 1470 formed by sheets 1430 and 1440 of the interior device, is used in conjunction with a selectable collection of heat dissipating pads 1710, 1720, 1730 with a variety of indentation force deflection (IFD) ratings to provide a highly customizable degree of comfort and protection for the device wearer.

Figure 15:
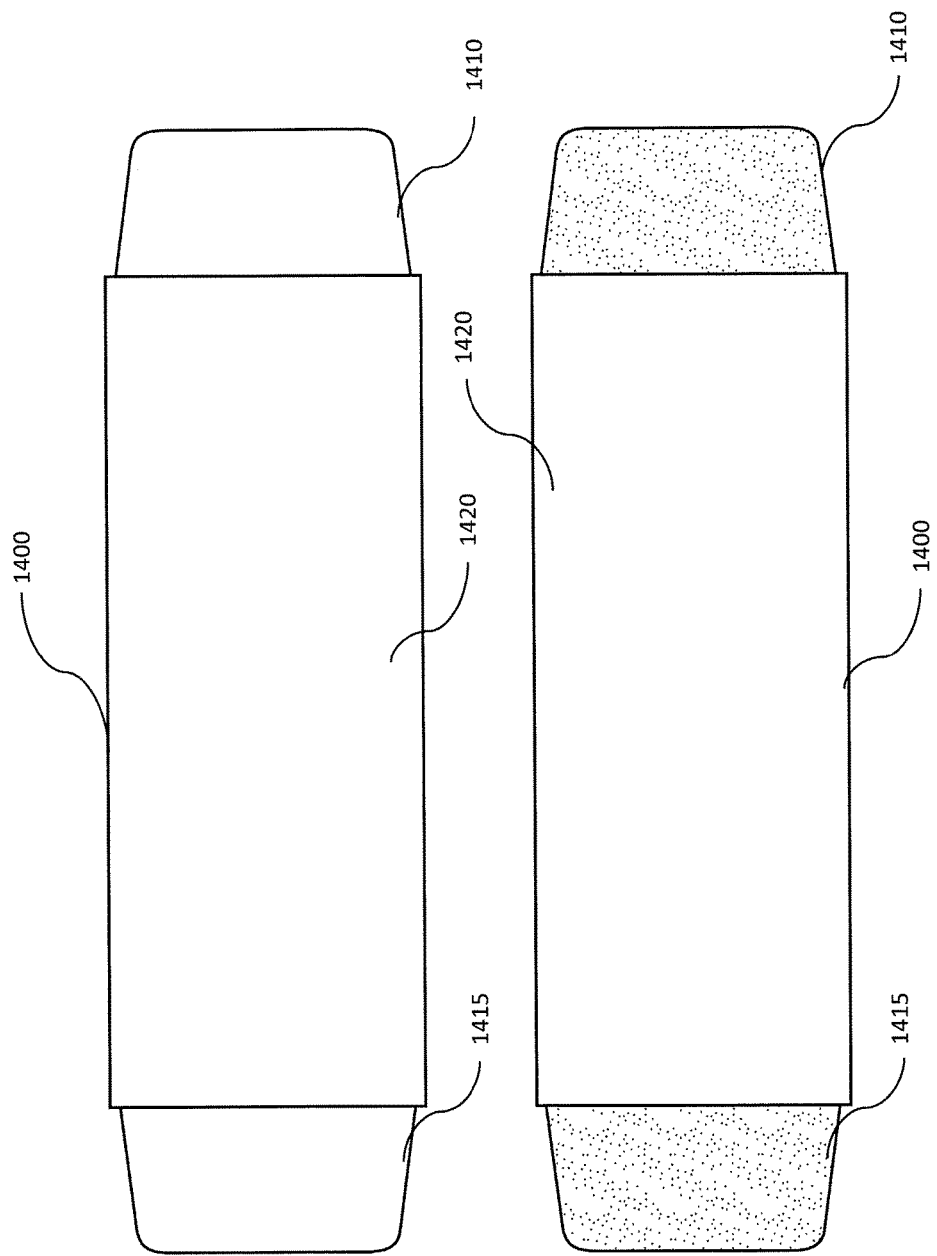
FIG. 15 illustratively depicts two straps laying on opposite sides to indicate the locations of the patches/tabs on the ends of the flexible straps containing, on one side, filamentary fastening hooks that are configured to releasably engage a complimentary looped fabric material of the device cover.

Turning to FIG. 15, two views are provided of the opposing sides of the flexible elastic wrap 1400 depicted in FIG. 14a and FIG. 14b. A filamentary hook material of the patch 1410 and a filamentary hook material of the patch 1415 are attached on opposite ends of a flexible strap 1420. The wrap 1400 enables wearers to secure the device cover structure (see FIGS. 14a and 14b) around a knee joint by affixing the filamentary fastening hook tabs 1410 and 1415 attached on ends of the flexible elastic wrap 1400 anywhere on the unbroken loop fabric exterior of the device cover structure depicted in FIGS. 14a and 14b. One end of the flexible elastic wrap 1400 with a filamentary fastening hook tab 1410 is attached to the device cover structure and an opposite end of the flexible elastic wrap 1400 with a filamentary fastening hook tab 1415 is attached to the exterior of the device cover structure after wrapping around the leg in accordance with the invention.

Figure 16:
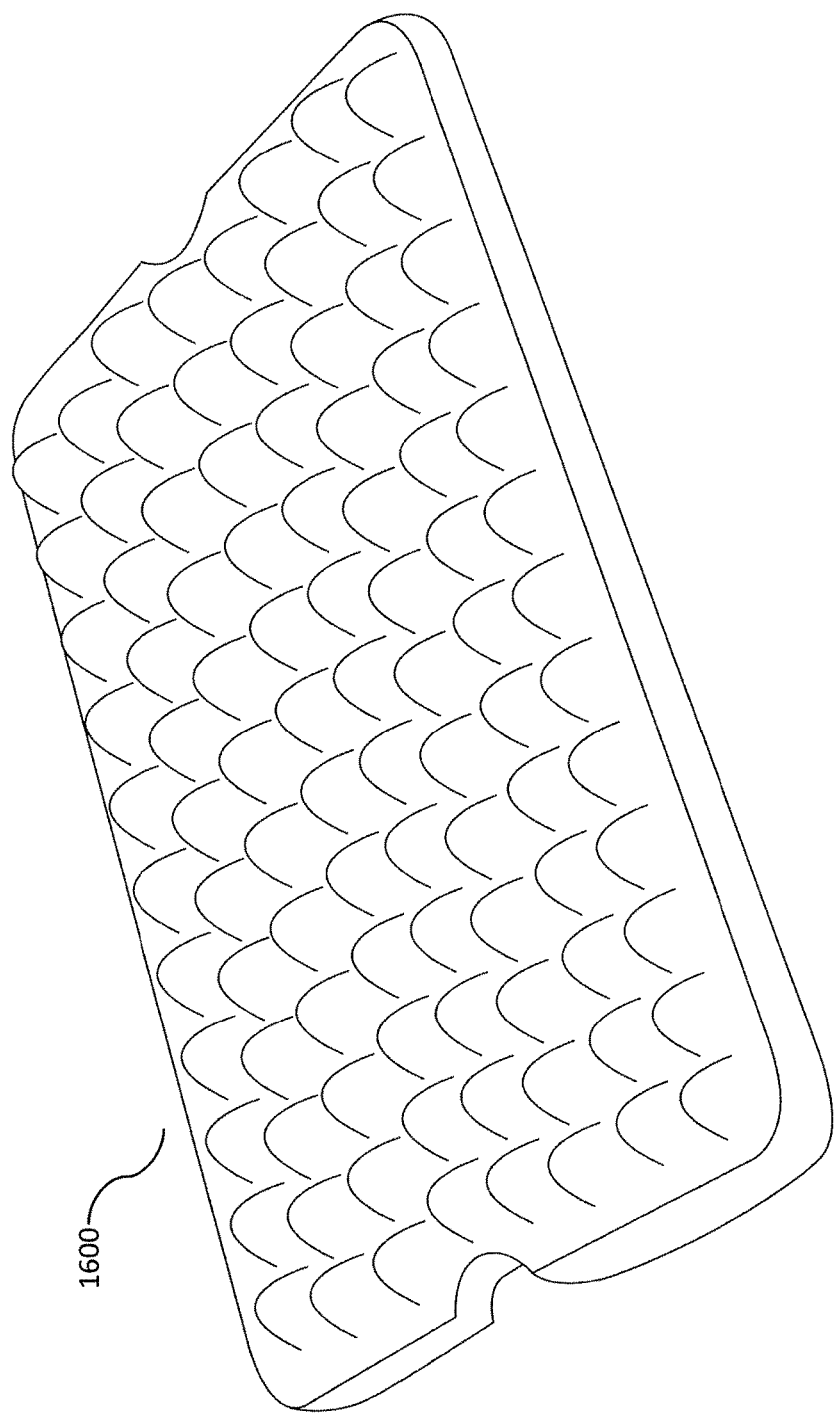
FIG. 16 illustratively depicts an isometric view of an exemplary (large) dimpled heat dissipating molded foam padding insert, including at least one convoluted surface comprising an array of concave and convex regions that form air gaps when the joint protection device is secured to a knee joint.

Turning to FIG. 16 an illustrative depiction provides an isometric top view of an exemplary heat dissipating molded pad 1600 with convoluted molded concave and convex indentation for patella and irregular shapes of the joint and leg, and for providing enhanced air circulation (in comparison to non-convoluted surfaces of molded padding) and comfort.

Turning to FIG. 17 an illustrative depiction provides isometric top views of three molded pads providing varying degrees of protection when inserted into the pocket of the joint protection device. The set includes a heat dissipating molded pad 1710 with convoluted molded concave and convex indentation for patella and irregular shape of the joint and leg for increased air circulation and comfort. The set further includes molded pads without convoluted surfaces to replace and/or augment the level of protection provided by molded pad 1710. A first supplemental molded pad 1720 is slightly thicker than a second supplemental molded pad 1730 providing enhanced customizability of a degree of padding/protection provided by the joint protection device.

Figure 20:
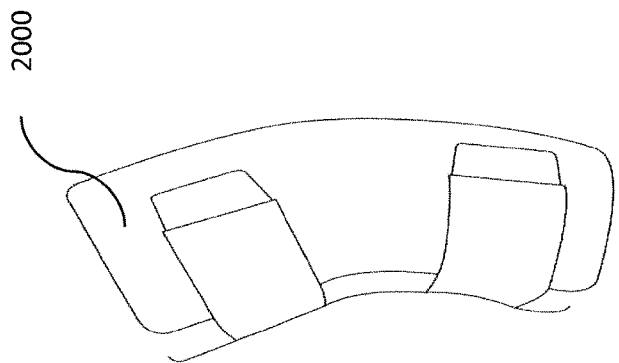
FIGS. 18, 19 and 20 illustratively depict three perspectives (front, rear and side) of the alternative embodiment of the joint protection device, including two detachable straps, in a secured position on a wearer's knee.
Figure 19:
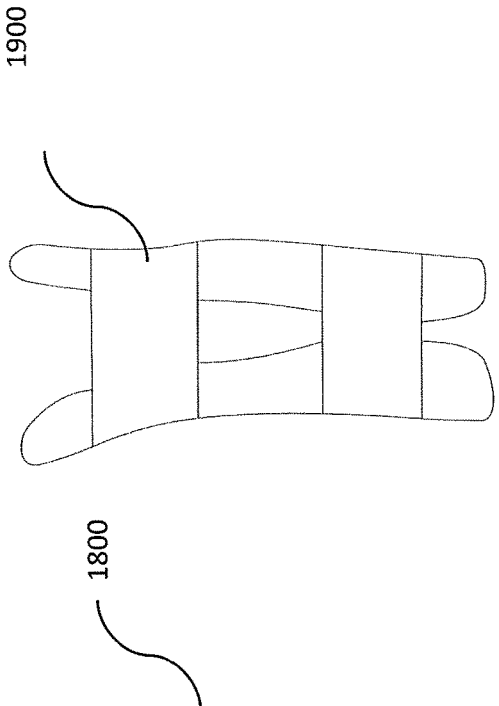
Figure 18:
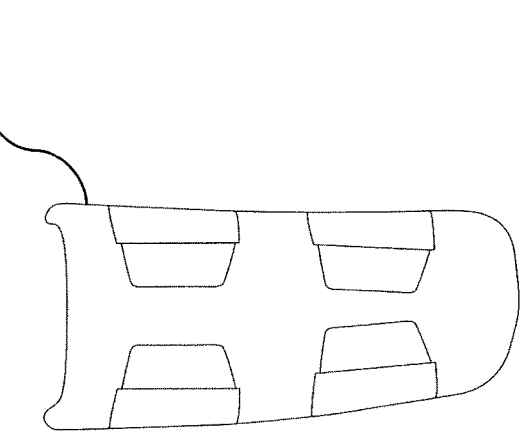

FIGS. 18, 19 and 20 depict a front view 1800, a rear view 1900 and a side view 2000 of the device depicted in FIGS. 14*a* and 14*b* when wrapped around a wearer's knee.

It is thus contemplated that other implementations of the invention may differ in detail from foregoing examples. As such, all references to the invention are intended to reference the particular example of the invention being discussed at that point in the description and are not intended to imply any limitation as to the scope of the invention more generally. All language of distinction and disparagement with respect to certain features is intended to indicate a lack of preference for those features, but not to exclude such from the scope of the invention entirely unless otherwise indicated.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A joint protection device for comfortably protecting a knee of a wearer while in a resting position, the joint protection device comprising:
   an interior device cover structure comprising a fabric sheet incorporating a ceramic fiber phase change material and having a moisture wicking property, wherein during use the interior device cover structure faces toward the knee of the wearer;
   an exterior device cover structure comprising unbroken loop fabric, wherein the exterior device cover structure and the interior device cover structure are joined along edges to form a pocket;
   a wrap for securing the joint protection device against a leg of the wearer; and
   at least one heat dissipating protective pad occupying the pocket such that while the joint protection device is secured against the knee of the wearer, the heat dissipating protective pad covers a substantial majority of the knee, but capable of extending less than a full knee circumference when fastened to the knee, to provide protection against forces exerted by external objects on the substantial majority of the knee while providing an opening for direct exposure to air,
   wherein the at least one heat dissipating protective pad occupying the pocket is configured to extend over a front and both sides of the knee of the wearer, such that the joint protection device may provide protection for the front and both sides of the knee.

2. The device of claim 1 wherein the at least one heat dissipating protective pad comprises multiple pads, including at least a convoluted foam pad and a flat pad.

3. The device of claim 2 wherein at least one of the at least one pads is made of a memory foam material.

4. The device of claim 1 wherein the wrap comprises a detachable wrap comprising a flexible strap having at least one tab permanently attached thereto, the at least one tab comprising filamentary hook fibers that engage the unbroken loop fabric of the exterior device cover structure to facilitate securing the device around the knee of the wearer.

5. The device of claim 4 wherein the flexible strap includes two tabs comprising filamentary hook fibers, each one of the two tabs being attached at a respective opposing end of the flexible strap.

6. The device of claim 1 wherein the fabric sheet comprises a first fabric sheet and a second fabric sheet arranged to have unattached overlapping edges that form a slot configured to permit inserting/removal of the at least one heat dissipating pad.

7. The device of claim 1 wherein the pad is a convoluted memory foam material.

8. The device of claim 1 wherein the pad is a memory foam material.

9. The device of claim 1 wherein the at least one heat dissipating protective pad is notched on each side to reduce compression forces on the pad when the knee bends.

10. The device of claim 1 wherein the at least one heat dissipating protective pad is provided in the form of a pad set for simultaneous insertion within the pocket, the pad set including: a convoluted memory foam pad, a first flat polyurethane foam pad having a first thickness, and a second flat polyurethane foam pad having a second thickness that is greater than the first thickness.

11. The device of claim 1 wherein the at least one heat dissipating protective pad is provided in the form of a pad set for simultaneous insertion within the pocket, the pad set including at least two distinct pads differing from one another in a property selected from the group of pad properties consisting of:
   indentation force deflection (IFD) rating,
   foam density, and
   foam thickness.

12. The device of claim 1, wherein the at least one heat dissipating protective pad is configured to align the at least one heat dissipating protective pad over the knee of the wearer in a resting position.

13. The device of claim 1, wherein the pocket formed by joined edges of the interior device cover structure and the exterior device cover structure facilitates slidable insertion and removal of the at least one heat dissipating protective pad from the pocket.

14. The device of claim 1, wherein the wrap comprises at least one end tab facilitating filamentary hook-based fastening of an end of the wrap to the unbroken loop fabric of the exterior device cover structure.

15. The device of claim 1, wherein the at least one heat dissipating protective pad comprises a molded pad made of a cushioning protective material configured to ensure against joint pressure points arising from contact with another object.

16. The device of claim 1, wherein the wrap is configured to secure the device to the knee of the wearer and maintain proper alignment and fixation of the device on the knee during bending of the knee.

17. The device of claim 1, wherein the wrap is a single strap structure that is wound multiple times around a leg of the wearer to form at least a first loop above the knee and a second loop below the knee.

18. The device of claim 1, wherein the at least one heat dissipating protective pad comprises a molded pad including a convex indentation to accommodate a patella of the wearer.

* * * * *